(12) United States Patent
Rutherford et al.

(10) Patent No.: US 7,461,423 B2
(45) Date of Patent: Dec. 9, 2008

(54) DEVICE FOR SUPPORTING AT LEAST ONE ARM OF AN OPERATING PERSON DURING A SURGICAL OPERATION

(75) Inventors: Ian Rutherford, Dundee (GB); Leslie Kelly, Cupar (GB); Stuart Brown, St. Andrews (GB); Timothy Graham Frank, Wormit Newport-On-Tay Fife (GB); Alfred Cuschieri, St. Andrews Fife (GB)

(73) Assignee: University of Dundee (GB)

( * ) Notice: Subject to any disclaimer, the term of this patent is extended or adjusted under 35 U.S.C. 154(b) by 365 days.

(21) Appl. No.: 11/297,241

(22) Filed: Dec. 8, 2005

(65) Prior Publication Data

US 2006/0186292 A1    Aug. 24, 2006

(30) Foreign Application Priority Data

Dec. 9, 2004    (EP)    ................... 04029169

(51) Int. Cl.
A61G 13/12    (2006.01)
(52) U.S. Cl. ................ 5/646; 5/623; 5/652; 5/657; 248/118; 248/278.1
(58) Field of Classification Search .............. 5/623, 5/646, 647, 503.1, 507.1, 652, 657; 248/278.1, 248/118
See application file for complete search history.

(56) References Cited

U.S. PATENT DOCUMENTS

| 1,025,476 | A | 5/1912 | Mellen |
| 1,474,304 | A | 11/1923 | Weber |
| 3,124,328 | A | 3/1964 | Kortsch |
| 3,436,046 | A | 4/1969 | Valeska |
| 4,390,011 | A | * 6/1983 | Evans ......................... 5/507.1 |
| 4,620,697 | A | 11/1986 | Pithon |
| 5,029,941 | A | 7/1991 | Twisselmann |
| 5,074,501 | A | 12/1991 | Holtta |
| 5,152,486 | A | * 10/1992 | Kabanek et al. ............. 248/201 |
| 5,281,001 | A | * 1/1994 | Bergsten et al. ........ 297/411.24 |
| 6,176,456 | B1 | 1/2001 | Wisniewski |
| 6,704,959 | B2 | * 3/2004 | Schuerch ....................... 5/648 |
| 6,925,668 | B2 | * 8/2005 | Cuschieri et al. ............... 5/623 |
| 2002/0100851 | A1 | 8/2002 | Abramowsky et al. |

FOREIGN PATENT DOCUMENTS

DE    195 04 838    2/1995

* cited by examiner

Primary Examiner—Michael Trettel
(74) Attorney, Agent, or Firm—St. Onge Steward Johnston & Reens LLC

(57) ABSTRACT

A device for supporting at least one arm of an operating person during a surgical or medical operation comprises at least one supporting element for supporting the at least one arm of the operating person, the supporting element being arranged at a carrying structure for carrying the at least one supporting element, wherein the carrying structure is configured such that the at least one supporting element can be lowered or raised for adjusting the height of the operating person's arm. The carrying structure comprises at least one carrying arm, which is pivotable about at least one at least approximately horizontal pivot axis such that pivoting of the carrying arm raises or lowers the at least one supporting element. The carrying structure further comprises a mechanical control system acting on the pivotability of the at least one carrying arm in the upward direction differently from the downward direction.

19 Claims, 6 Drawing Sheets

DEVICE FOR SUPPORTING AT LEAST ONE ARM OF AN OPERATING PERSON DURING A SURGICAL OPERATION

CROSS-REFERENCE TO RELATED APPLICATIONS

This application claims priority of European Patent Application No. 04 029 169.2 filed on Dec. 9, 2004.

BACKGROUND OF THE INVENTION

The invention relates to a device for supporting at least one arm of an operating person during a surgical or medical operation.

A device of the kind mentioned at the outset, which can also be designated as an arm rest, is used as a support of the surgeon's or the surgical assistant's arm during an operation in order to increase steadiness of movement and reduce fatigue. Taking into consideration that a surgical operation can take up several hours and the surgical personnel carries out such an operation in a standing position, an arm rest of the afore-mentioned kind will be effective in avoiding a loss of preciseness of the manipulations carried out by the operating person.

The supporting device comprises at least one supporting element for supporting the at least one arm of, for example, the surgeon. The supporting element is arranged at the carrying structure for carrying the at least one supporting element, wherein the carrying structure should be adapted to be mounted on a side of the operating table or in front of a surgical stool. However, the carrying structure of the device according to the invention can also be configured as a self-standing structure which can stand on the floor of the operating room beside the operating table.

In particular, an arm rest is very useful in complex laparoscopic surgery which requires precise movements, and usually long execution times of the operating person. Discomfort in the shoulders, back and neck is an established complaint amongst laparoscopic surgeons and is related to the unnatural postures adopted during laparoscopic intervention. Discomfort, and the associated fatigue, is a contributory factor in the execution of errors. A supporting arm rest provides the benefit of avoiding such disadvantages.

A device known from DE 195 04 838 A1 is a supporting device integrated into an operating stool which can also be integrated in the operating table. The operating stool comprises an adjustable arm rest supporting the arms or hands of the surgeon leading over the operating area.

However, in that document it is not disclosed how to adjust the height of the supporting element and, accordingly, the surgeon's or surgical assistance's arm or hand.

SUMMARY OF THE INVENTION

Therefore, it is an object of the present invention to provide a device of the kind mentioned at the outset which allows a person the arm of which is supported by the at least one supporting element, to easily adjust the height of the at least one supporting element. The adjustment of the at least one supporting element should not distract the operating person from the surgical operation.

According to an aspect of the invention, a device for supporting at least one arm of an operating person during a surgical or medical operation is provided, comprising at least one supporting element for supporting the at least one arm of the operating person, a carrying structure for carrying the supporting element at which the supporting element is arranged, the carrying structure being configured such that the at least one supporting element can be lowered or raised for adjusting a height of the operating person's arm, the carrying structure having at least one carrying arm which is pivotable about at least one at least approximately horizontal pivot axis such that pivoting of the carrying arm raises or lowers the at least one supporting element, and the carrying structure comprising a mechanical control system acting on the pivotability of the at least one carrying arm in the upward direction differently from the downward direction.

With the supporting device according to the invention, adjusting of the height of the at least supporting element and thereby the operating person's arm is accomplished by the fact that the supporting element is carried on at least one carrying arm which is pivotable about an at least approximately horizontal pivot axis. Thus, the device according to the invention allows high changes of the operating person's arm to be made during use with minimal interference to the actions of the operating person. Further, according to the invention, a mechanical control system is provided which acts on the at least one carrying arm by controlling the pivotability of the at least one carrying arm in the upward direction differently from the downward direction. Such a mechanical control system can be provided with mechanical structural parts which are very simple in terms of cost and manufacturing.

In a first kind of embodiments of the present invention, raising the supporting element is very easily achieved by lifting the supporting element thus pivoting the carrying arm in upward direction, by exerting a pulling force on the supporting element, and lowering the supporting element is achieved by exerting a pushing force on the supporting element thereby pivoting the carrying arm in downward direction.

In this context, it is preferred, if the control system imposes a first friction to the pivotability in the upward direction and a second friction to the pivotability in the downward direction, wherein the second friction is higher than the first friction.

In this embodiment, the mechanical control system is configured very simple as a passive system. The user of the device just pushes on the supporting element to lower the supporting element, wherein the pushing force must be greater than the second friction imposed to the pivotability of the carrying arm by the mechanical control system. Raising the supporting element is simply achieved by lifting the supporting element in upward direction. The friction imposed to the pivotability of the carrying arm in downward direction should be chosen such that it is higher than the normal supporting force exerted by the user when his or her arm rests on the supporting element.

In this context, it is preferred, if the second friction increases during downward movement of the carrying arm.

The advantage of this measure is that the increasing friction when moving the supporting element downwards increases the stability of the carrying structure and avoids collapsing or sudden lowering of the supporting element thus avoiding the risk of failures.

In a further preferred embodiment, the control system further comprises at least one damper for limiting the speed of the downward movement of the carrying arm.

This measure has the advantage that the damper provides further protection against an undesired rapid descent of the supporting element in the event of failure of the device.

In a further preferred embodiment, the first friction and the second friction are adjustable.

It is advantageous herewith that the first and second frictions which have to be exceeded for lowering or raising the supporting element, can be set by the user according to his or her needs.

In a further preferred embodiment, the first friction is smaller than about 10 N, preferably is about 0.

By virtue of this measure raising the supporting element does not require large pulling forces, but only the weight of the supporting element and the carrying arm has to be exceeded in order to raise the supporting element.

In a further preferred embodiment, the control system includes a rotary joint through which the carrying arm is pivotable about the pivot axis, wherein the rotary joint is at least approximately freely rotatable in one direction, and is rotatable in the opposite direction only when applying a downward force on the supporting element which is higher than a preset frictional force.

In this way, the mechanical control system can be easily included in the rotary joint itself thus lowering the number of structural parts and the costs of the supporting device.

In a preferred embodiment, such a rotary joint can comprise a ratchet-pawl-mechanism, wherein the ratchet is freely rotatable with respect to the carrying arm when the carrying arm is raised, and wherein the pawl engages the ratchet and the ratchet is rotatable only with the second friction, when the carrying arm is lowered.

For example, the ratchet can be clamped onto a shaft which does not co-rotate with the carrying arm, while the pawl then is fixed to the carrying arm. The second friction which has to be exceeded to lower the supporting element can be adjusted, for example, by adjusting the clamping force of the clamp on the shaft.

In another preferred embodiment the rotary joint can comprise a one-way free wheel clutch bearing.

In a second kind of embodiments, the control system comprises a locking mechanism for locking the pivotability in the downward direction, wherein the locking mechanism is releasable for lowering the supporting element.

The advantage of this kind of embodiment is the increased safety of the device with respect to undesired descents of the supporting element, because an undesired lowering of the supporting element is securely avoided by locking the pivotability of the carrying arm in the downward direction. In order to lower the supporting element, the locking mechanism is releasable in a controlled manner.

In this context it is preferred, if the locking mechanism is releasable by slightly lifting the supporting element.

Differently from the first kind of embodiments described above, the lowering of the supporting element is initiated by first slightly lifting the supporting element, whereby the locking mechanism is released so that the supporting element can be lowered in the released state of the locking mechanism. Raising of the supporting element is achieved by lifting the supporting element with a greater force. The advantage of this measure is that releasing of the locking mechanism is very easily achieved by simply slightly raising the supporting element.

In a further preferred embodiment, the locking mechanism is reactivated after having been released by exerting a pushing force onto the supporting element which exceeds the force for lowering the supporting element.

The advantage of this measure is that the pivotability of the carrying arm is locked again after having adjusted the desired height of the supporting element in a very easy manner by just exerting a pushing force onto the supporting element. The force for lowering the supporting element preferably is the weight of the supporting element and the carrying arm carrying the supporting element.

In this context, it is further preferred, if the control system further comprises a damper for limiting the downward speed of the at least one carrying arm.

The advantage of this measure is that the downward motion can be better controlled and allows the user to press down the supporting element against a resistance and thereby to reactivate the locking mechanism for locking the pivotability again.

In a structural simple embodiment, the at least one carrying arm comprises a first articulated parallelogram, which is pivotable about the horizontal axis, and wherein the locking mechanism locks the pivotability of this first parallelogram.

Preferably, the first parallelogram comprises a first parallelogram arm to which a first locking element is connected, and a second parallelogram arm to which a second locking element is connected, the first and second locking elements being displaceable with respect to one another in the unlocked state and immovable with respect to one another in the locked state.

Further, the locking mechanism preferably comprises a third locking element, wherein the third locking element is movable between the locking position and an unlocking position, wherein the third locking element restrains the relative displacement between the first and second locking elements when in its locking position and allows the relative displacement between the first and second locking elements when in its unlocking position.

The at least one carrying arm preferably comprises a second articulated parallelogram articulatedly connected to the first parallelogram and connected to the supporting element, and wherein the third locking element is connected to the second parallelogram.

The afore-mentioned embodiments provide a structural very simple locking mechanism for locking and unlocking the pivotability of the carrying arm in downward direction.

As an alternative embodiment, the locking mechanism comprises a ratchet-pawl-arrangement for locking the pivotability of the carrying arm in downward direction.

Differently to the above-mentioned embodiment which also uses a ratchet-pawl-arrangement which allows downward motion of the carrying arm against a high frictional force, the present embodiment provides a locking of the downward motion of the carrying arm in a desired height position.

Further features and advantages will be apparent from the following description and the accompanying drawings.

It is to be understood that the features mentioned before and those features yet to be explained hereinafter are not only applicable in the given combination, but also in other combinations or in isolation without departing from the scope of the present invention.

BRIEF DESCRIPTION OF THE DRAWINGS

Exemplary embodiments of the invention are shown in the drawings and will be explained below with reference to the drawings. In the drawings.

DETAILED DESCRIPTION OF THE INVENTION

Figure 1:
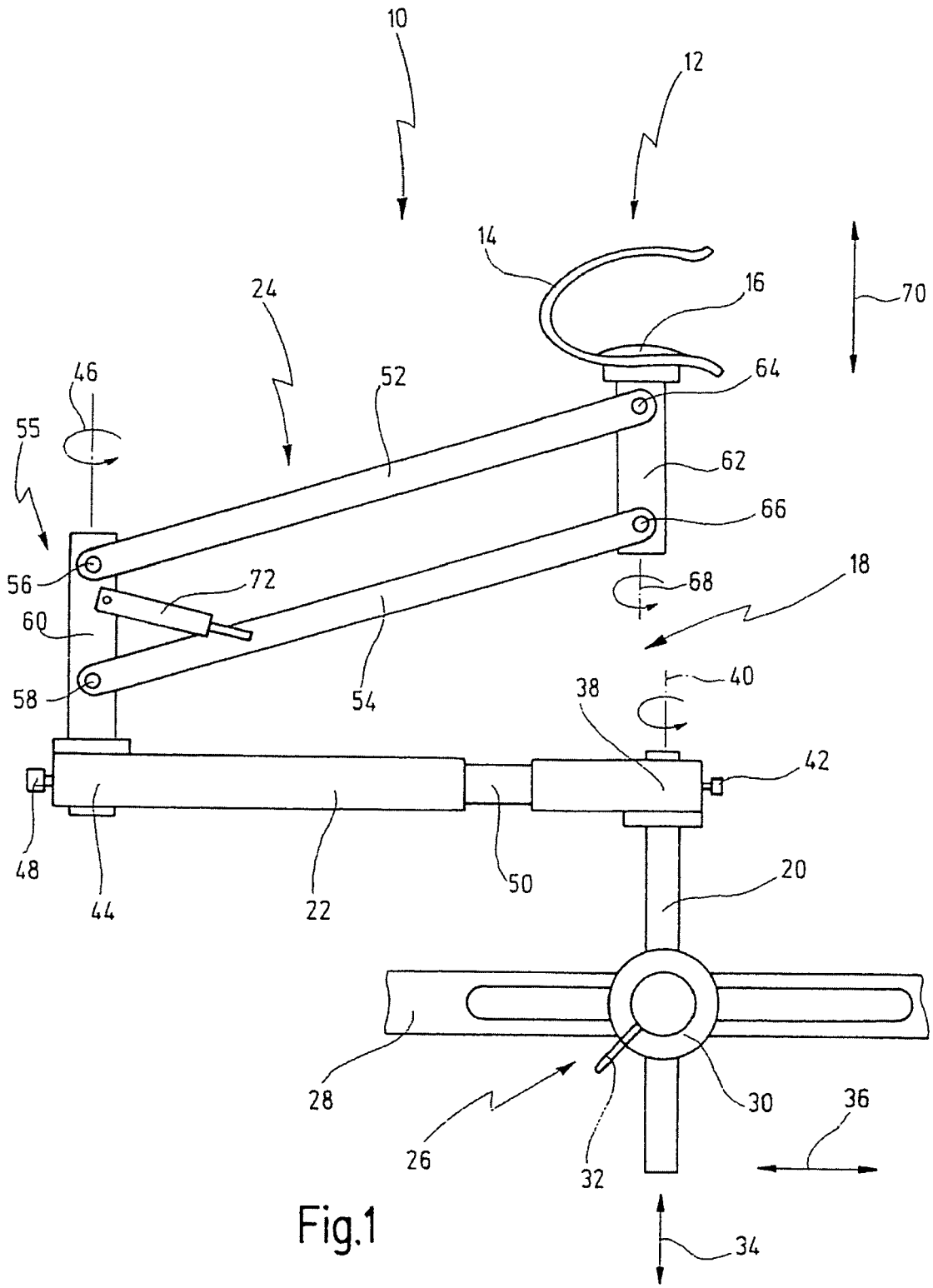
FIG. 1 schematically shows a device for supporting at least one arm of an operating person in a side view showing the general design of the device.

FIG. 1 shows a device labeled in its entirety with reference numeral 10 for supporting at least one arm of an operating person (not shown) during a surgical or medical operation.

The device 10 can be used for all surgical disciplines, but is in particular useful for laparoscopic or other endoscopic procedures.

The device 10 comprises at least one supporting element 12 for supporting at least one arm of, for example, the surgeon or surgical assistant.

The supporting element 12 comprises a C-shaped element 14 in which the operating person's forearm in the region between the wrist and the elbow can be accommodated. A contact pad 16 of the supporting element 12 provides for a better comfort to the operating person.

The supporting element 12 is arranged at a carrying structure 18 for carrying the at least one supporting element 12.

The carrying structure 18 comprises a first carrying arm 20 extending vertically or substantially vertically, a second carrying arm 22 connected to the first carrying arm 20 and extending horizontally or substantially horizontally, and a third carrying arm 24 connected to the second carrying arm 22. The supporting element 12 is connected to the third carrying arm 24.

The third carrying arm 24 will be described in more detail below.

The device 10 further comprises a mounting portion 26 for mounting the device 10 to an underlying support structure 28 which is, for example, an operating table or operating stool. The mounting portion 26 comprises an adjustable mounting bracket 30 receiving the first carrying arm 20. The mounting bracket 30 comprises a bracket lock 32 for locking the carrying arm 20 in a desired position to the underlying support structure 28. After releasing the bracket lock 32, the carrying arm 20 can be adjusted in height according to a double arrow 34 for a rough height adjusting of the entire device 10. Further, after releasing the bracket lock 32, the carrying arm 20 can also be displaced in horizontal direction according to a double arrow 36. Furthermore, after releasing the bracket lock 32 it is also possible to lift up the first carrying arm 20 and thereby the entire device 10 out of the mounting bracket 30 for removing the device 10 from the underlying structure.

The first carrying arm 20 is connected with the second carrying arm 22 via a joint 38 so that the carrying arm 22 can be rotated clockwise or counter-clockwise about a vertical or substantially vertical rotation axis 40. The rotation of the second carrying arm 22 is preferably possible over a full angle of 360°.

A friction adjuster 42 is provided in order to adjust the friction opposing the rotary movement of the second carrying arm 22 about the rotation axis 40.

The third carrying arm 24 is connected with the second carrying arm 22 via a further joint 44 allowing rotation of the third carrying arm 24 about a further vertical or substantially vertical rotation axis 46 in clockwise or counter-clockwise direction, and preferably over a full angle of 360°. A further friction adjuster 48 is provided in order to adjust the friction of the joint 44 so that the force necessary to move the first carrying arm 24 about the rotation axis 46 can be adjusted to the operating person's needs.

The second carrying arm 22 is optionally provided with a length adjustment, for example by configuring the second carrying arm 22 as a telescopic arm as indicated by reference numeral 50.

The third carrying arm 24 is configured, according to the embodiment in FIG. 1, as a parallelogram, which comprises a first parallelogram arm 52 and a second parallelogram arm 54 which are spaced from one another in vertical direction. The first and second parallelogram arms 52 and 54 are preferably configured as pairs of parallelogram arms in each case, i.e. there are further parallelogram arms arranged parallel to the parallelogram arms 52 and 54 in a plane behind the plane of the drawing in FIG. 1.

The third carrying arm 24 as a whole is pivotable about an at least approximately horizontal pivot axis 55, and in the configuration of the third carrying arm 24 as a parallelogram, there is a pivot axis 56 for the parallelogram arm 52 and a pivot axis 58 for the parallelogram arm 54.

The pivot axes 56 and 58 are provided at a vertical post 60 connected to the second carrying arm 22.

The supporting element 12 is connected to the third carrying arm 24, i.e. to the parallelogram arms 52 and 54 via a further vertical post 62 to which the parallelogram arms 52 and 54 are also pivotably connected via pivot axes 64 and 66. The supporting element 12 is rotatably connected to the post 62 so that the supporting element 12 can be rotated about a vertical or substantially vertical rotation axis 68 relative to the carrying structure 18.

By pivoting the third carrying arm 24 about the pivot axis 55, i.e. more exactly about the pivot axes 56 and 58, the supporting element 12 which is carried by the third carrying arm 24, can be lowered or raised according to a double arrow 70.

Optionally, a bias force element 72 can be provided which biases the third carrying arm 24 in the upward direction or in the downward direction, if desired.

Figure 2:
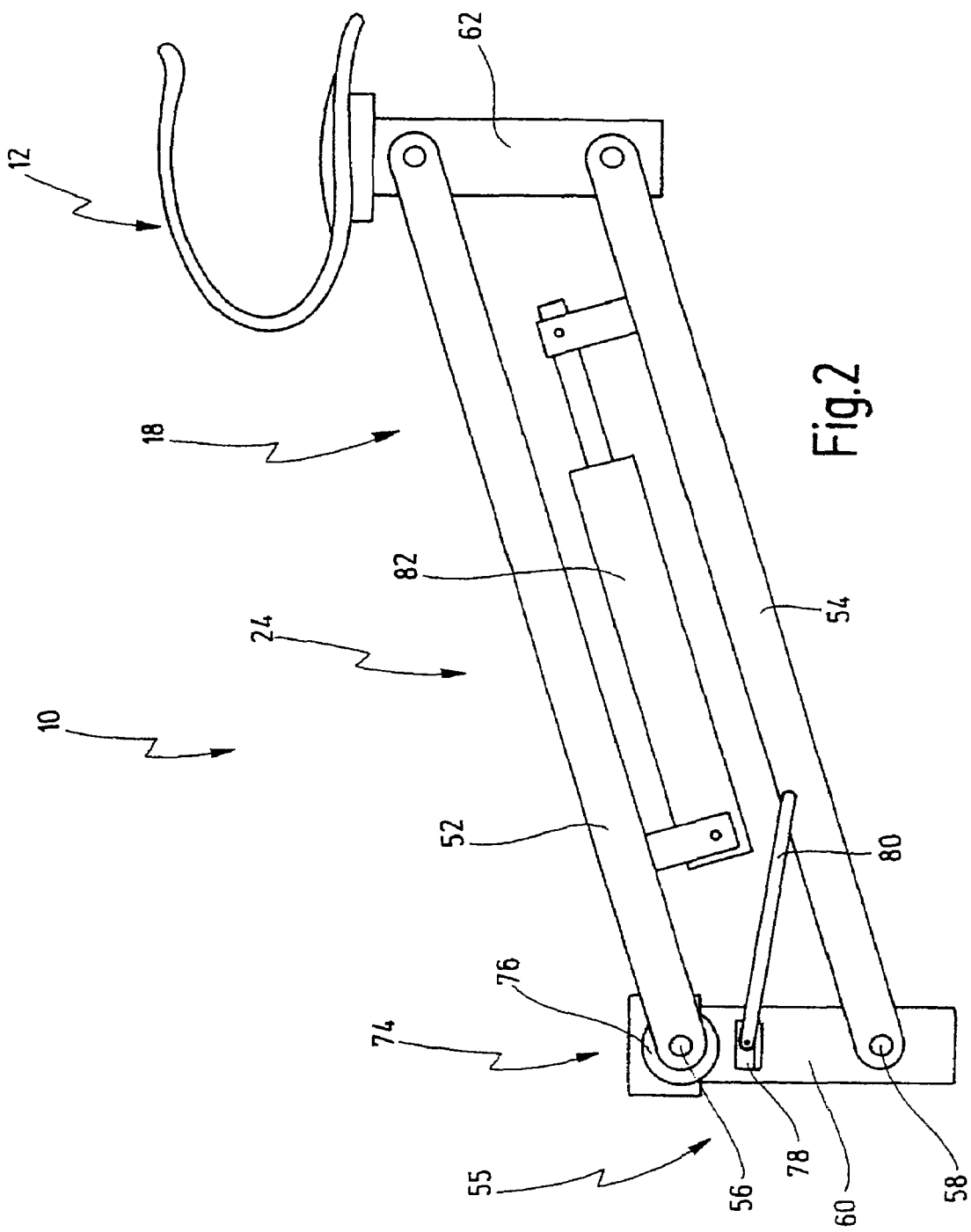
FIG. 2 shows a part of a device for supporting at least one arm in a partial view according to a first embodiment.

With reference to FIG. 2, a first embodiment of a mechanical control system is described which acts on the pivotability of the carrying arm 24 in the upward direction differently from the downward direction. FIG. 2 shows the device 10 in FIG. 1 in a partial view in which only the supporting element 12 and the third carrying arm 24 are shown. Further, FIG. 2 shows further elements of the device 10 which have been omitted in FIG. 1.

A mechanical control system 74 as mentioned before serves to control the downward and upward motion of the carrying arm 24 and thereby the supporting element 12. In this embodiment, the control system 74 imposes a first friction to the pivotability of the carrying arm 24 in the upward direction and the second friction to the pivotability in the downward direction, wherein the second friction is higher than the first friction. Thus, in order to lower the supporting element 12, the operating person just has to exert a pushing force with his or her arm accommodated in the supporting element 12 which is high enough in order to exceed the high second friction. In order to raise the supporting element 12, the operating person just has to lift his or her arm in the supporting element 12 against the first friction which is preferably a low friction.

This kind of control mechanism is accomplished in the embodiment of FIG. 2 in that the parallelogram arm 52 is hinged to the vertical post 60 via a rotary joint, which is for example a one-way rotary joint, for example a free wheel clutch bearing. Such a one-way rotary joint can be formed, for example, by an inner and an outer cylinder, wherein rotation of the inner cylinder with respect to the outer cylinder is inhibited in one direction and free in the other direction. The inner cylinder can be fixed to the parallelogram arm 52, while the outer cylinder is housed rotatably in the vertical post 60. The rotation in downward direction is restrained by an adjustable friction path, which is shown in FIG. 2 with reference numeral 78. Thus, a second friction which has to be exceeded for lowering the supporting element 12, can be adjusted according to the user's needs.

Further, it can be provided that the second friction increases during downward movement of the carrying arm 24. According to the embodiment in FIG. 2, this is accomplished by a rod 80 one end of which is connected to the parallelogram arm 54 and the other end of which is connected to the friction adjuster 78. Thus, when the carrying arm 24 is pivoted in downward direction, the rod 80 continuously sets the friction adjuster 78 to higher frictions.

Further, in the embodiment shown in FIG. 2, a damper 82 is provided which limits the speed of the downward movement of the carrying arm 24.

The additional damping of the downward movement of the carrying arm 24 acts as an additional protection against an undesired rapid descent of the supporting element 12 in the event of a failure of the rotary joint.

Preferably, the pulling force required for raising the supporting element 12 by just lifting the supporting element 12 is not substantially larger than the weight of the supporting element and the part of the carrying structure 18 in the region of the carrying arm 24, i.e. the first friction of the pivotability of the carrying arm 24 is as small as possible, preferably zero.

On the other hand, the second friction which opposes the downward movement of the carrying arm 24, should be higher than the weight of the supporting element 12 and the carrying structure 18 in the region of the carrying arm 24 and, in addition, the force exerted by the operating person's arm when leaning on the contact pad 16 for carrying out a surgical procedure.

Figure 3:
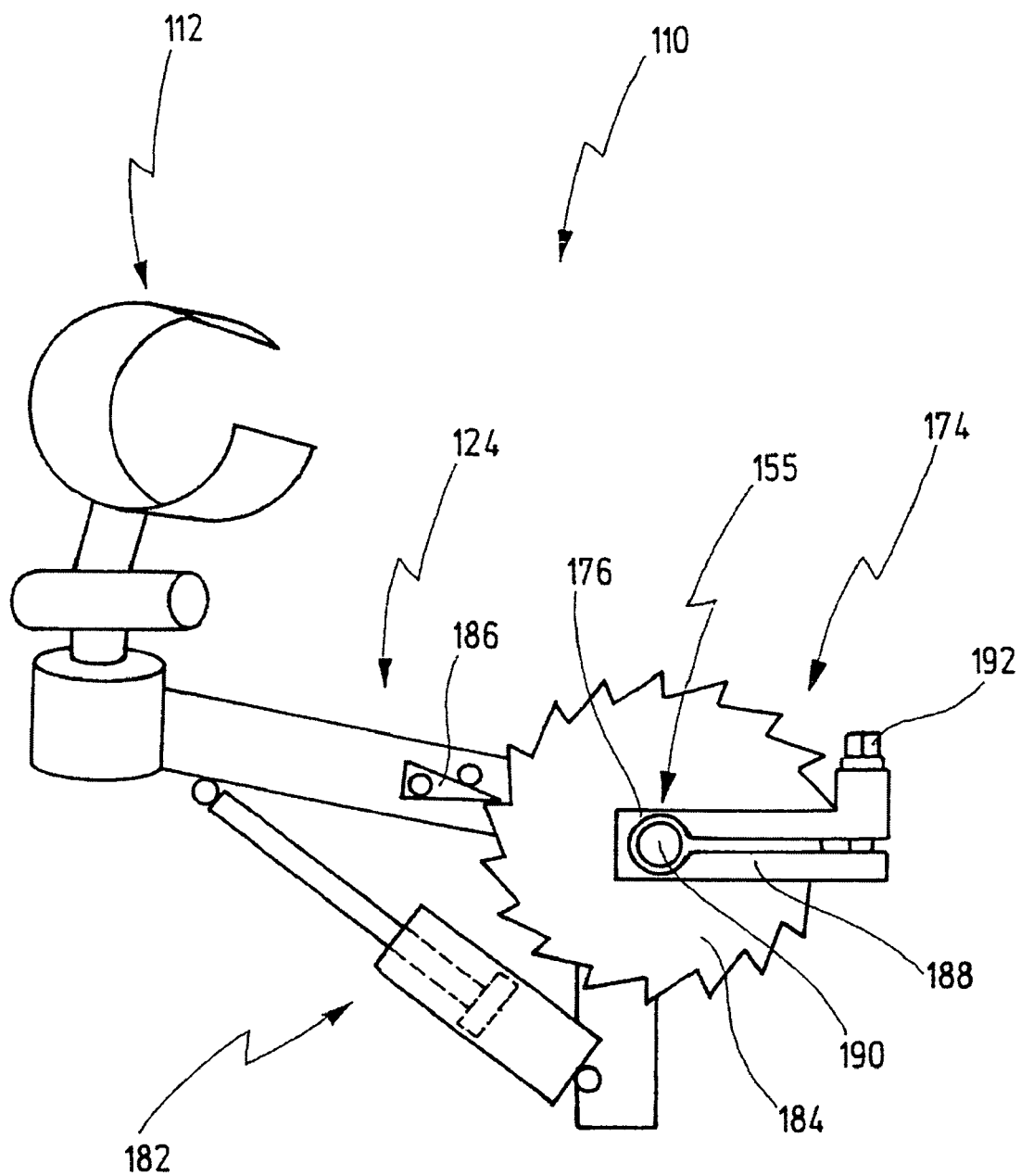
FIG. 3 shows a part of a device for supporting at least one arm according to another embodiment.

FIG. 3 shows another embodiment of a device for supporting at least one arm of an operating person during a surgical or medical operation, wherein the device is only shown in the region of the supporting element and the carrying arm carrying the supporting element. Those parts which are identical or similar or comparable with parts of the embodiment shown in FIG. 2 are referenced by the same reference numeral raised by 100. The carrying arm 24 is formed by one bar only in this case but it is also possible to provide the parallelogram design as in FIG. 2 here or vice versa.

The embodiment shown in FIG. 3 is based on the same control principle for lowering or raising the supporting element 112 as in the previous embodiment. This means that lowering the supporting element 112 is performed by exerting a pushing force onto the supporting element 112 with a strength exceeding the second friction opposed to the pivotability of the carrying arm 124 in the downward direction, while the supporting element 112 is raised by exerting a pulling force on the supporting element 112 which is opposed a lower frictional force which preferably is zero.

Instead of the one-way free wheel clutch bearing of the mechanical control system 74 in FIG. 2, the control system 174 comprises a rotary joint 176, which comprises a ratchet-pawl-mechanism. The ratchet-pawl-mechanism comprises a ratchet 184 in form of a toothed wheel and a pawl 186.

The ratchet 184 is clamped by means of a clamp 188 to a shaft 190 the axis of which coincides with the pivot axis 155 of the carrying arm 124. The clamping force of the clamp 188 can be adjusted by a screw 192.

When the supporting element 112 is raised, the carrying arm 124 pivots in clockwise direction about a pivot axis 155 and the pawl 186 clicks over the teeth of the ratchet 184 which does not co-rotate but is fixed by the clamp 188. The distance between the single teeth of the ratchet can be made small, so to allow raising the supporting elements quasi-continuously. For lowering the supporting element 112, a pushing force has to be exerted on the supporting element 112 which must be larger than the friction between the shaft 190 and the clamp 188 which forms the second friction in the afore-mentioned sense. By adjusting the clamping force of the clamp 188 on the shaft 190 by setting the screw 192, the operating person can control the second friction according to his or her needs.

Figure 4:
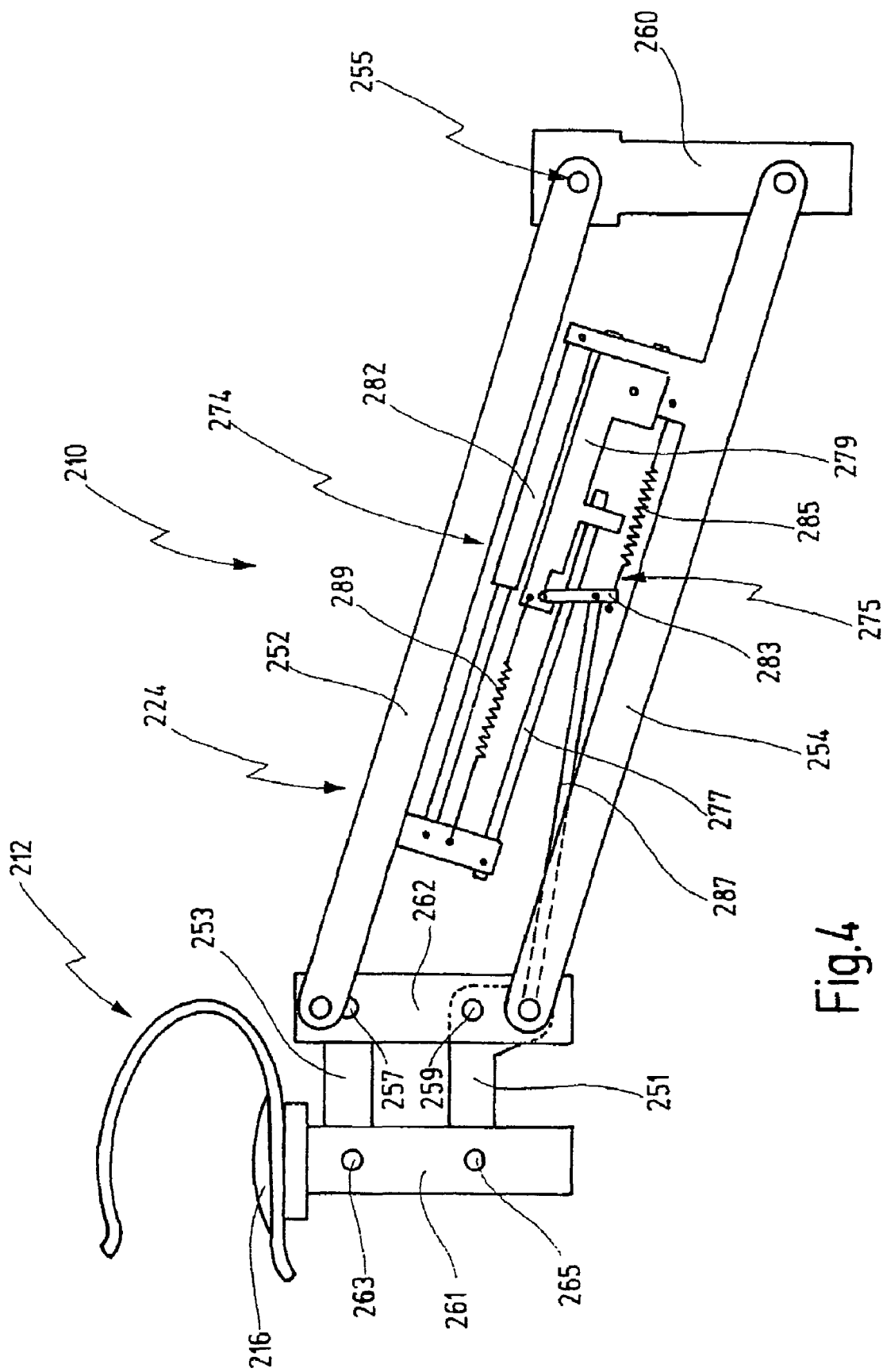
FIG. 4 shows a part of a device for supporting at least one arm according to another embodiment in a first operational state.
Figure 5:
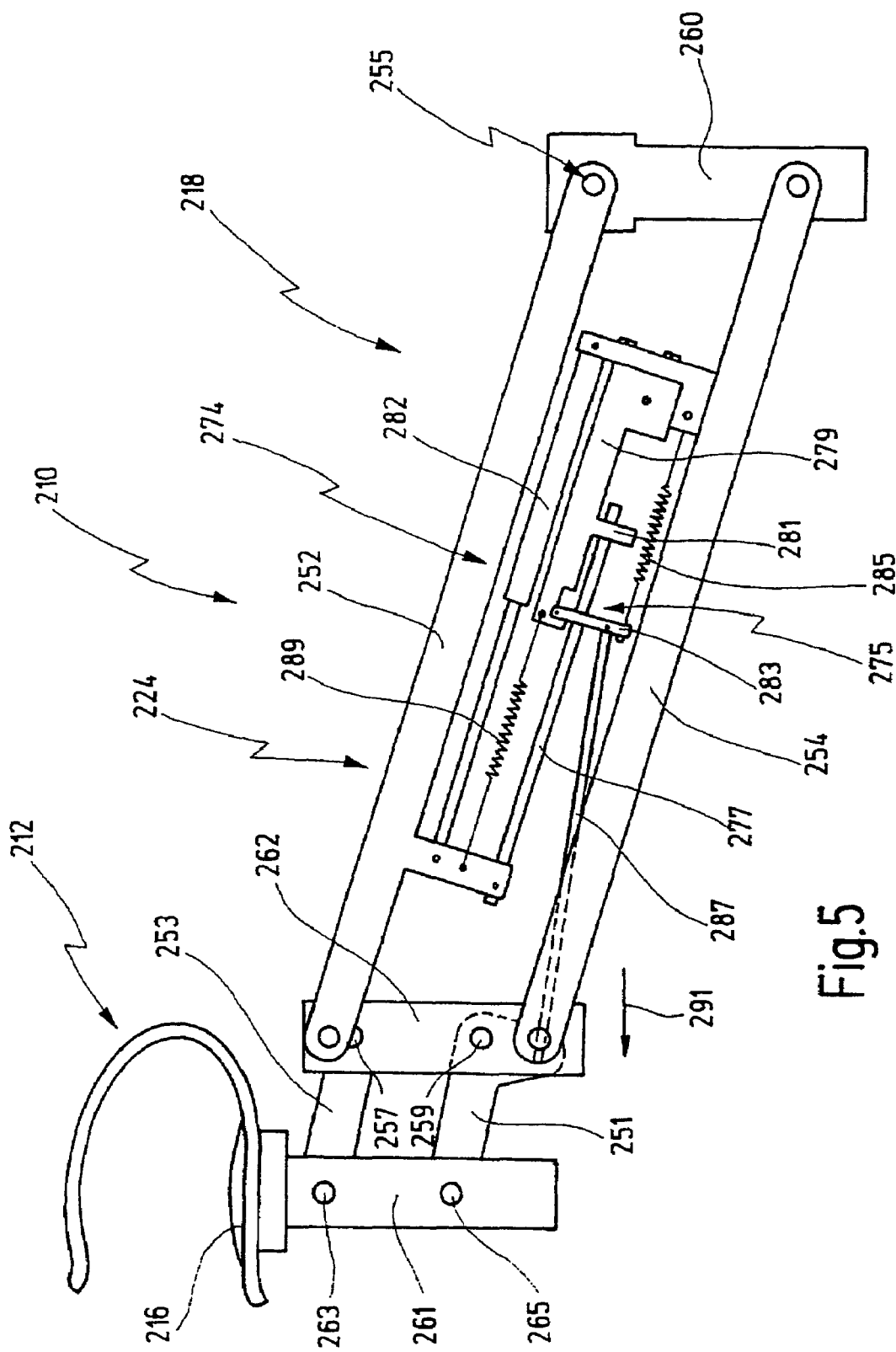
FIG. 5 the device in FIG. 4 in a second operational state.

FIGS. 4 and 5 show another embodiment of a device 210 for supporting at least one arm of an operating person during a surgical or medical operation which is shown like the embodiments in FIGS. 2 and 3 only in the region of the supporting element 212 and the carrying arm 224 of the carrying structure 218. Again, those parts of the device 210 which are identical, similar or comparable with the parts of the device 10 are labeled with the same reference numerals raised by 200.

The carrying arm 224 is configured as a first parallelogram comprising the parallelogram arms 252 and 254. Differently from the embodiment shown in FIG. 2, the supporting element 212 is connected to the vertical post 262 by a second parallelogram comprising parallelogram arms 253, 251 which are hinged to the vertical post 262 via pivot axes 257, 259 and to another vertical post 261 via pivot axes 263 and 265.

In this embodiment, the mechanical control system 274 comprises a locking mechanism 275 for locking the pivotability of the carrying arm 224 in the downward direction and which is releasable for lowering the supporting element 212 if such a lowering is to be carried out.

The locking mechanism comprises a first locking element 277 which is fixedly connected to the first (upper) parallelogram arm 252 of the carrying arm 224. A second locking element 279 is fixedly connected to the second (lower) parallelogram arm 254 of the carrying arm 224. The first locking element 277 which is configured as a rod, passes through a bore in an extension 281 of the second locking element 279.

The locking mechanism 275 further comprises a third locking element 283 which is movable between a locking position shown in FIG. 4 and an unlocking position shown in FIG. 5. The third locking element 283 is formed as a plate having a bore therethrough through which the first locking element 277 passes.

In the unlocking position of the third locking element 283, the first locking element 277 is displaceable relative to the second locking element 279. In the locking position of the third locking element 283, as shown in FIG. 4, the third locking element 283 prevents a relative displacement between the first locking element 277 and the second locking element 279.

The third locking element 283 is biased into its locking position of FIG. 4 via a spring 285.

Further, the third locking element 283 is connected via a rod 287 to the parallelogram arm 251 of the second parallelogram at a location which is spaced apart from the pivot axis 259. For this purpose, the parallelogram arm 251 is substantially L-shaped.

Further, the first parallelogram arm 252 of the carrying arm 224 is connected to the second parallelogram arm 254 of the first parallelogram of the carrying arm 224 in spring-loaded fashion by means of a main bias spring 289.

The function of the control system 274, in particular of the locking mechanism 275 is as follows.

FIG. 4 shows the device 210 in the operational state where the downward pivotability of the carrying arm 224 is locked, because the third locking element 283 is in its locking position. The operating person's arm can rest on the contact pad 216 without the risk of a descent of the supporting element 212. If the operating person wishes to lower the supporting element 212, it has to release the locking mechanism 275 by slightly lifting the supporting element 212 which is performed by lifting the arm accommodated in the supporting element 212 against the upper portion of the C-shaped supporting element 212. When the supporting element 212 is slightly lifted, the second parallelogram (parallelogram arms 253 and 251) distorts causing the L-shaped parallelogram 255 to pivot about the pivot axis 259. The pivoting of the parallelogram arm 251 about the pivot axis 259 pulls the rod 287 in direction of an arrow 291 in FIG. 5 thereby moving the third locking element 283 from its locking position into its unlocking position shown in FIG. 5 against the force of the spring 285. Thus, the locking mechanism 275 is released.

The spring tension of the spring 285 should be adjusted such that the lifting force required to release the locking mechanism 275 is substantially less than that required to raise the carrying arm 224 against the combined effect of the weight of the supporting element 212 and the carrying arm 224 and the load of the main biased spring 289. The main biased spring 289 biases the carrying arm 224 in the downward movement direction.

Now, after the locking mechanism 275 having been released, the supporting element 212 can be lowered by pivoting the carrying arm 224 about the pivot axis 255. Lowering of the supporting element 212 is performed without the need of exerting an additional pushing force onto the supporting element 212, because of the supporting element 212 and the carrying arm 224 together with the main biased spring 289 effects the lowering of the carrying arm 224 without the need of additional pushing forces.

In order to be able to reactivate the locking mechanism 275, a damper 282 is provided which limits the speed of the downward movement of the carrying arm 224 about the pivot axis 255. The damper 282 enables the operating person to reactivate the locking mechanism 275 by exerting a short pushing force pulse onto the supporting element 212 thus bringing the second parallelogram (parallelogram arms 251 and 253) back in their original position, thereby pushing the rod 287 and moving the third locking element 283 from the unlocking position in FIG. 5 to the locking position in FIG. 4.

Figure 6:
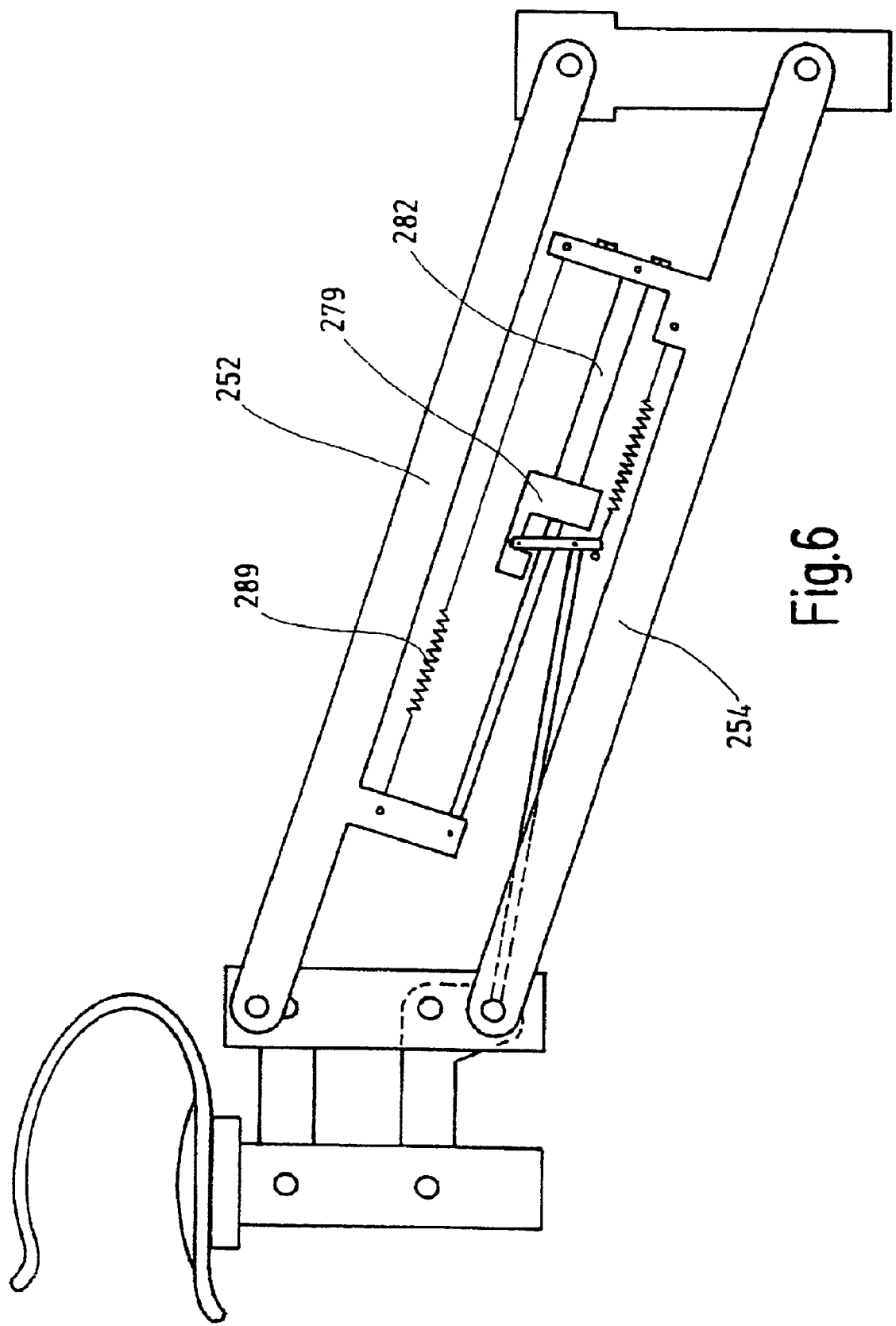
FIG. 6 shows a part of a device for supporting at least one arm according to another embodiment similar to the embodiment of FIGS. 4 and 5.

FIG. 6 shows another embodiment which is very similar to the embodiment shown in FIGS. 4 and 5 so that the same reference numerals have been used for this embodiment as in the previous embodiment.

The difference between the embodiment shown in FIG. 6 and the embodiment shown in FIGS. 4 and 5 is that the damper 282 and the second locking element 279 are combined in one structural component thus reducing the number of parts of that embodiment with respect to the previous embodiment. The function of the embodiment shown in FIG. 6, however, is the same as in the embodiment shown in FIGS. 4 and 5.

While FIGS. 4 through 6 show embodiments in which the locking mechanism is configured as a locking strut mechanism, it could be envisaged to configure the locking mechanism also by a ratchet-pawl-arrangement similar to the embodiment shown in FIG. 3, however with the difference that the ratchet-pawl-mechanism does not allow a downward movement of the carrying arm by overcoming a preset frictional force, but the ratchet-pawl-mechanism has to be released in order to initiate the lowering of the supporting element.

What is claimed is:

1. A device for supporting at least one arm of an operating person during a surgical or medical operation, comprising:
    at least one supporting element for supporting said at least one arm of said operating person,
    a carrying structure for carrying said supporting element at which said supporting element is arranged, said carrying structure being configured such that said at least one supporting element can be lowered or raised for adjusting a height of said operating person's arm,
    said carrying structure having at least one carrying arm which is pivotable about at least one at least approximately horizontal pivot axis such that pivoting of said carrying arm raises or lowers said at least one supporting element, and
    said carrying structure comprising a mechanical control system acting on the pivotability of said at least one carrying arm in the upward direction differently from the downward direction, wherein said control system imposes a first friction to said pivotability in said upward direction and a second friction to said pivotability in said downward direction, wherein said second friction is higher than said first friction.

2. The device of claim 1, wherein said supporting element comprises a substantially C-shaped element for accommodating said operating person's arm therein.

3. The device of claim 1, wherein said second friction increases during downward movement of said carrying arm.

4. The device of claim 1, wherein said control system further comprises at least one damper for limiting the speed of the downward movement of said carrying arm.

5. The device of claim 1, wherein at least one of said first friction and said second friction is adjustable.

6. The device of claim 1, wherein said first friction is smaller than about 10 N.

7. The device of claim 6, wherein said first friction is about 0.

8. The device of claim 1, wherein said control system comprises a locking mechanism for locking said pivotability in the downward direction, wherein said locking mechanism is releasable for lowering said supporting element.

9. A device for supporting at least one arm of an operating person during a surgical or medical operation, comprising:
    at least one supporting element for supporting said at least one arm of said operating person,
    a carrying structure for carrying said supporting element at which said supporting element is arranged, said carrying structure being configured such that said at least one supporting element can be lowered or raised for adjusting a height of said operating person's arm,
    said carrying structure having at least one carrying arm which is pivotable about at least one at least approximately horizontal pivot axis such that pivoting of said carrying arm raises or lowers said at least one supporting element, and
    said carrying structure comprising a mechanical control system acting on the pivotability of said at least one carrying arm in the upward direction differently from the downward direction wherein said control system includes a rotary joint through which said carrying arm is pivotable about said pivot axis, wherein said rotary joint is at least approximately freely rotatable in one direction, and is rotatable in the opposite direction only when applying a downward force on said supporting element which is higher than a preset frictional force.

10. The device of claim 9, wherein said rotary joint comprises a ratchet-pawl-mechanism, a ratchet of said ratchet-pawl-mechanism being freely rotatable with respect to said carrying arm when said carrying arm is raised, and wherein a pawl of said ratchet-pawl-mechanism engages said ratchet and said ratchet is rotatable only with friction, when said carrying arm is lowered.

11. The device of claim 9, wherein said rotary joint comprises a one-way freewheel clutch bearing.

12. A device for supporting at least one arm of an operating person during a surgical or medical operation, comprising:
   at least one supporting element for supporting said at least one arm of said operating person.
   a carrying structure for carrying said supporting element at which said supporting element is arranged, said carrying structure being configured such that said at least one supporting element can be lowered or raised for adjusting a height of said operating person's arm,
   said carrying structure having at least one carrying arm which is pivotable about at least one at least approximately horizontal pivot axis such that pivoting of said carrying arm raises or lowers said at least one supporting element, and
   said carrying structure comprising a mechanical control system acting on the pivotability of said at least one carrying arm in the upward direction differently from the downward direction, wherein said control system comprises a locking mechanism for locking said pivotability in the downward direction, wherein said locking mechanism is releasable for lowering said supporting element by slightly lifting said supporting element.

13. The device of claim 12, wherein said locking mechanism is reactivated after having been released by exerting a pushing force onto said supporting element which exceeds the force for lowering said supporting element.

14. The device of claim 13, wherein said control system further comprises a damper for limiting the downward speed of said at least one carrying arm.

15. The device of claim 12, wherein said at least one carrying arm comprises a first articulated parallelogram, which is pivotable about said pivot axis, and wherein said locking mechanism locks said pivotability of said first parallelogram.

16. The device of claim 15, wherein said first parallelogram comprises a first parallelogram arm to which a first locking element is connected, and a second parallelogram to which a second locking element is connected, said first and second locking elements being displaceable with respect to one another in an unlocked state and immovable with respect to one another in a locked state.

17. The device of claim 16, wherein said locking mechanism further comprises a third locking element, wherein said third locking element is movable between a locking position and an unlocking position, wherein said third locking element restrains a relative displacement between said first and second locking element when said third locking element is in a locking position and allows a relative displacement between said first and second locking elements, when said third locking element is in an unlocking position.

18. The device of claim 17, wherein said at least one carrying arm comprises a second articulated parallelogram articulatedly connected to said first parallelogram and connected to said supporting element, and wherein said third locking element is connected to said second parallelogram.

19. The device of claim 12, wherein said locking mechanism comprises a ratchet-pawl-arrangement for locking the pivotability of said carrying arm in downward direction.

* * * * *